United States Patent
Fournel et al.

(10) Patent No.: US 8,990,029 B2
(45) Date of Patent: Mar. 24, 2015

(54) DEVICE FOR THE CENTRALIZED MANAGEMENT OF MEASUREMENTS AND DATA RELATING TO THE LIQUID AND GAS FLOWS NEEDED FOR THE OPERATION OF A COMBUSTION ENGINE

(75) Inventors: Johan Fournel, Robion (FR); Alain Lunati, La Fare les Oliviers (FR)

(73) Assignee: SP3H, Aix en-Provence (FR)

( * ) Notice: Subject to any disclaimer, the term of this patent is extended or adjusted under 35 U.S.C. 154(b) by 1063 days.

(21) Appl. No.: 12/675,247

(22) PCT Filed: Aug. 14, 2008

(86) PCT No.: PCT/FR2008/001194
§ 371 (c)(1),
(2), (4) Date: Jun. 4, 2010

(87) PCT Pub. No.: WO2009/056709
PCT Pub. Date: May 7, 2009

(65) Prior Publication Data
US 2010/0305827 A1    Dec. 2, 2010

(30) Foreign Application Priority Data
Aug. 31, 2007 (FR) ........................... 07 06140

(51) Int. Cl.
| | |
|---|---|
| *G01N 21/33* | (2006.01) |
| *G01M 15/08* | (2006.01) |
| *G01N 21/3504* | (2014.01) |
| *G01N 21/3577* | (2014.01) |
| *G01M 15/10* | (2006.01) |
| *G01N 21/359* | (2014.01) |

(52) U.S. Cl.
CPC ............. *G01N 21/33* (2013.01); *G01M 15/108* (2013.01); *G01N 21/3504* (2013.01); *G01N 21/3577* (2013.01); *G01N 21/359* (2013.01)
USPC ........................................................... 702/50

(58) Field of Classification Search
CPC .... G01N 21/33; G01N 21/3577; G01M 15/08
USPC .............. 702/28, 30, 50; 250/339.12, 339.13;
73/114.71, 114.73; 701/108, 109
See application file for complete search history.

(56) References Cited

U.S. PATENT DOCUMENTS

| | | | | |
|---|---|---|---|---|
| 5,225,679 | A * | 7/1993 | Clarke et al. .................. | 250/343 |
| 6,629,453 | B1 * | 10/2003 | Surnilla et al. ............. | 73/114.73 |
| 7,143,575 | B2 * | 12/2006 | Pizzi ............................... | 60/285 |
| 2004/0201835 | A1 * | 10/2004 | Coates et al. ................... | 356/73 |

* cited by examiner

*Primary Examiner* — Manuel L Barbee
(74) *Attorney, Agent, or Firm* — Arent Fox LLP

(57) ABSTRACT

The invention relates to a device for the centralized management of measurements and data relating to liquid and/or gas flows needed for the correct operation of a combustion engine controlled by an engine computer and/or of a vehicle, said device comprising means for analyzing at least two liquid and/or gas flows including at least one light source, at least one optical signals detector and at least one system for analyzing the detected signals. At least one of said analysis means is used to analyze two of said flows. In this way, this device minimizes the bulk and added mass incurred by the analytical methods employed to analyze the various flows and simplifies the management of such a system.

18 Claims, 3 Drawing Sheets

DEVICE FOR THE CENTRALIZED MANAGEMENT OF MEASUREMENTS AND DATA RELATING TO THE LIQUID AND GAS FLOWS NEEDED FOR THE OPERATION OF A COMBUSTION ENGINE

CROSS-REFERENCED TO RELATED APPLICATION

This application is a National Stage entry of International Application No. PCT/FR2008/001194, filed Aug. 14, 2008, which claims priority to French patent application Ser. No. 07/06140, filed Aug. 31, 2007, the disclosure of the prior application is incorporated in its entirety by reference.

BACKGROUND

1. Field

The invention relates to a device for the centralized management of measurements and data relating to the liquid and gas flows needed for the correct operation of a combustion engine and/or a vehicle.

2. Introduction

Combustion engines use a plurality of flows more particularly fuel, engine lubrication oil, engine cooling fluid, brake fluid for the vehicles, the liquids participating in the post-treatment of the polluting emissions (urea solution for neutralizing nitrogen oxides for example serine for the regeneration of the additive particulate filter).

The combustion of the air/fuel mixture in a combustion engine entails emissions of greenhouse effect gas (carbon dioxide) and pollutants (unburnt hydrocarbons, carbon monoxide, nitrogen oxides, particles, aldehydes).

The always stricter regulations relating to the emissions of greenhouse effect gas as well as to the polluting emissions entail always more important efforts for engine manufacturers. The taking into consideration, by the engine computer, of the quality of the various liquid and/or gas flows, such as fuel, inlet air, exhaust gas and the fluids needed for the various post-treatment steps in particular tends to generalise, so as to optimise combustion engines with the aim of minimizing the consumption of fuel and thus the greenhouse effect exhaust gas as well as the polluting emissions during the whole life of the combustion engine and/or the vehicle provided with a combustion engine.

It is known that the quality of fuels has a direct influence on performances, consumption, polluting emissions and greenhouse effect exhaust gas.

A. DOUAUD has proved, as from 1983, for controlled ignition engines, the connection between the quality of gasoline, the adjustments of the engine and the occurrence of the knocking phenomenon. J. C. GUIBET, as from 1987, in the reference book Carburants et Moteurs proved the interactions between the quality of the fuel and the engine and the influence thereof in the engine combustion setting and adjustment models. More recently, in 1997, in a publication, A. GERINI analyzes the sensitivity to the gasoil parameters of a direct injection diesel engine on a vehicle. Eventually, in 2003, N. HOCHART provided a modelling of pollutant emissions of present engines using gasoline, diesel for light vehicles or trucks, by varying the quality of fuel by modifying the refining bases used in the mixtures.

The composition and the quality of fuels, although it is defined by standards and more particularly standards EN 590 and EN 228 in Europe, vary over time. Quality changes as a function of deliveries, distributors, seasons and prevailing regulations. It is thus estimated that the physico-chemical properties of fuels can vary from 15 to 40% or more around the average values defined in the standards. As antipollution standards are always stricter, there a need to determine the quality of fuel and to take the same in consideration while adjusting the engine parameters such as injection, combustion and post-treatment parameters. The qualitative measurement of fuel and the use thereof by the engine computer are more particularly examined in documents WO9408226, U.S. 2004000275, FR-2542092, U.S. Pat. No. 5,126,570, U.S. Pat. No. 5,262,645, U.S. Pat. No. 5,239,860 and WO2006100377.

With the same goal of limiting polluting emissions, methods describing engine control parameters adjustments as a function of the onboard analysis of exhaust gas, document WO02095376 can be cited, which describes a modular structure method enabling the detection and characterisation of liquid and solid particles and gas constituents of exhaust gas which can be used to adjust the engine and the structural elements for exhaust gas.

Some post-treatment methods include the utilization of reagent fluids or catalysts. The system of conversion of nitrogen oxides by a reaction with a urea solution and the method converting particles using a liquid additive can be more particularly cited. Such methods require the addition of additional storage tanks, the volume and mass of which increase the constraints of bulk and the mass of the combustion engine and/or of the vehicle. Managing at best the utilization of such fluids thus become a strategy so as to minimize the bulk and added mass. To ensure the efficiency of such post-treatment methods, the quality of catalysts and reagents implied in such methods is of utmost importance; it is legitimate to consider measuring the quality thereof using an onboard system.

In spite of the regulatory or internal provisions recommended by fuel distributors and vehicle manufacturers, such as refiners and distributors' quality improvement procedures, the display of the nature of fuels at the filling stations, the diameter of the dispensing nozzle and the diameter of the tank filling system in particular, many users willingly or not introduce a non-adapted fuel into the tanks of their vehicles. An increasing number of vehicles is used with products which are not certified by the manufacturers and the customs services like used frying oils, non-esterified vegetable oils, domestic fuel oils, causing important damages to the power unit, the fuel supply system and the post-treatment system. The damages (fouling of injectors, of the engine, of the tank, choking of the filters, seizing of the pumps, deactivation of catalysts) can be severe, severely impact the engine injection and combustion phases and increase the regulated or not polluting emissions, which can lead to the engine break. Similarly, some fuels such as water/gasoil or gasoline/alcohol or gasoil/bio-fuels emulsions can be instable and the quality thereof can deteriorate over time (storage stability, phenomenon of de-mixing between gasoline and ethanol or gasoil and diester above 5%). Such various sources of deterioration of the nature of the fuel potentially entail an increase in the vehicle pollution, damages to the vehicle or at least important corrective operations. Thus, concepts and methods aim at providing preventive safety to the elements of the power unit of a vehicle equipped with a combustion engine, prior to or during the ignition phase further to deterioration of the nature of the fuel contained in the tank and the fuel supply system. Such concepts and systems involve the measurement of the fuel quality, ideally in the fuel supply system.

For example, the method described in document FR0607420 aiming at providing safety to the elements of the power unit further to the detection of the fuel deterioration can be mentioned.

Post-treatment methods such as a diesel particulate filter in particular contain catalysts which are particularly sensitive to sulphur compounds.

Such sulphur compounds, as a matter of fact, make catalysts less active and also affect the efficiency of the methods for converting post-treatment polluting emissions. The law very significantly reduced the maximum sulphur content of fuels; more particularly diesel today in Europe has a sulphur content of less than 50 ppm and the future legislation will reduce this sulphur content to less than 10 ppm.

Such specifications on the sulphur content in fuels make it possible for the post-treatment methods sensitive to sulphur compounds to extend their lives and the duration of correct operation thereof. This also makes it possible for such post-treatment methods to progress by making it possible to use more and more developed catalysts that have an increased sensitivity to sulphur compounds. Engine lubrication oils, due to their design, contain high sulphur compound contents. During the operation of the engine, a part of such sulphur compounds existing in the engine lubrication oil can participate in the combustion and thus circulate along the post-treatment line. Such sulphur compounds initially existing in the lubrication oil thus participate, as those from the fuel, in the deactivation of post-treatment catalysts. Thus, in order to provide an efficient and extended post-treatment, it is important to follow the quality of oil and the evolution thereof over time. Thus, the quality of the lubrication oil must be taken into account by the engine computer and the optimisation of post-treatment.

The method described in details in document KR20020049612 disclosing a system for measuring the quality of the engine oil using spectroscopic methods can be mentioned.

The extension of guarantees provided by the engine manufacturers leads the latter to make the combustion engines more robust, and thus to inform, as soon as possible and as best as they can, the user or the companies in charge of servicing the vehicles, of the need for possible maintenance operations on the combustion engine or the vehicle.

As a matter of fact, to provide such guarantees, it is legitimate for the manufacturers to make sure that the utilization of the combustion engine and/or of the vehicle is complying and that the servicing operations inherent in the correct operation of the combustion engine and/or of the vehicle such as lubrication oil changes, brake fluid changes or cooling fluid changes are carried out at the frequency recommended by the manufacturers.

In addition, to provide a long term support of the engine user, the manufacturer more and more often supplies the latter with real time information on the condition of the engine and the next maintenance operations. The mile countdown displayed on the dashboard of some vehicles to inform the user of the number of kilometers to be covered prior to the next lubrication oil change operation, can be cited. It can be considered to supply the user or the engine maintenance companies with other real time information relating to the quality of the brake fluid for a vehicle and the engine cooling fluid, for example. Therefore, it becomes important to measure the quality of such fluids and to follow the evolution thereof over time. Conventional methods consist in measuring the glycol content existing in the cooling fluid and the refraction index makes it possible to characterize the quality of the brake fluid in a vehicle.

The measurement and tracking of the quality of each one of such fluids needed for the correct operation of a combustion engine and more particularly fuel, exhaust gas, lubrication oil, cooling fluid and brake fluid for a vehicle can be carried out using various analyzing techniques. Spectroscopic and in particular infrared, near infrared, ultraviolet and visible spectroscopic methods, electric conductivity and refraction index can more particularly be mentioned.

Each one of such systems for measuring the quality of the various fluids enabling a better management of the engine parameters, for example aboard a vehicle, must meet precise criteria such as resistance to vibrations or resistance to important temperature variations. Such systems must be conditioned so as to be able to operate under severe environments (dust, soot, smoke).

In addition, it shall be necessary to develop as many physical and connector technology interfaces with the engine computer as qualitative analyses of each flow, analyzed separately.

In addition, it is advisable to consider measuring the quality of some flows at various places; as a matter of fact, the measurement of qualitative exhaust gas can be carried out upstream or downstream of the post-treatment methods with a particular view to ensuring the correct operation of said methods.

Similarly, it is advisable to carry out the measurement of the fuel quality in the fuel supply pipe and in the fuel line supplying the engine: the first location will make it possible to ensure the compliance of the fuel introduced into the tank with the optional aim of warning the user or to protect the power unit; the second location of the measurement of quality will mainly enable the optimization of the engine control parameters.

Finally and more particularly for the systems aboard vehicles, the bulk and mass are important constraints; as a matter of fact, the space available in a tourist vehicle is particularly limited and any increase in the mass of a vehicle more particularly induces increases in the consumption of fuel.

SUMMARY

Thus, implementing a plurality of systems for the analysis of quality of the various fluids multiplies the difficulty of integration in the engine or the vehicle and induces an increase in the mass of the equipped vehicle.

The invention aims at remedying such problems by providing a device for the centralized management of measurements and data relating to the liquid and/or gas flows needed for the correct operation of a combustion engine.

For this purpose and according to a first aspect, the invention relates to a device for the centralized management of measurements and data relating to the liquid and/or gas flows needed for the correct operation of a combustion engine controlled by an engine computer, said device including means for analyzing at least two liquid and/or gas flows including at least one light source, at least one optical signals detector and at least one system for analyzing the detected signals, said device being characterized in that at least one of said analysis means is used for analyzing two of said flows.

Thus, some functionalities belonging to each system for the quality analysis of fluids needed for the correct operation of a combustion engine are grouped to remedy problems of bulk, integration and mass increase.

Advantageously, the analysis means are positioned on a unique platform.

Preferably, the device includes a unique communication interface with said engine computer, the physical and/or digital connector technology to the engine computer being common with the analysis means. Thus, the device according to the invention is easily installed and built in a vehicle.

Advantageously, the analysis means are ultraviolet, visible or near infrared spectroscopic means. Preferably, the spectroscopic analysis is continuous or discontinuous and carried out within the wavelength range between 190 nm and 2,500 nm.

The near infrared technology has numerous advantages and can more particularly be used for characterizing all the fluids needed for the correct operation of a combustion engine in a vehicle. Since the end of the 70s, many books on chemometry and publications give a theory on near infrared spectroscopy, the instruments and the methods to be implemented to develop liquid properties correlation and prediction models from the near infrared spectra thereof, from mathematics and statistics models.

The above-mentioned documents WO9408226, WO2006100377, WO02095376 and KR20020049612 show that the quality of fuels, engine lubrication oil, exhaust gas can be characterized by near infrared spectroscopy. Some characteristics of these fluids can on the other hand be characterized by visible and ultraviolet spectroscopy.

The sulphur content of a hydro-carbonated liquid is currently measured using ultraviolet spectroscopy.

The document WO2007006099 describes a method for characterizing organic fluids using coupled visible and near infrared spectroscopy.

According to the works by Hassoun P., Fabre D., Bastianelli D., Bonnal L., Bocquier F. in 2005 "Utilization of polyethylene glycol 6000 (PEG) as a faecal marker measured with Near Infra Red Spectrometry (NIRS) in sheep", the near infrared technology is adapted to the determination of the glycol content in a solution.

The studies carried out by Peter Snoer Jensen, Sren Ladefoged, Jimmy Bak, Stefan Andersson-Engels, Stefan Andersson-Engels, Lennart Friis-Hansen "Online monitoring of urea concentration in dialysate with dual-beam Fourier-transform near-infrared spectroscopy" show that the near infrared spectroscopy is adapted to the determination of the urea content in a solution.

Generally, the reference works for the near infrared such as the one by L. G. WEYER published in 1985 or the "Handbook of near infrared analysis" published in 1992 show that the near infrared technology can be applied for characterizing organic compounds; the fluids needed for the correct operation of a combustion engine due to the composition thereof can thus be all characterized by such near infrared technology. In addition, the near infrared technology has the advantage of not requiring a step of dilution of the sample and to be a non-destructive analysis method.

Finally, the near infrared makes it possible to use the same wavelength range to collect the near infrared spectra of various liquid and gas products; the length of the optical path (length of the sample gone through by the light flow) alone varies. As a matter of fact, the length of the optical path for the determination of the quality of a gas will be significantly greater than the length of the optical path used for characterizing a liquid according to the Beer Lambert law.

The near infrared technology combined with that of the optical fibres offers many optical architecture possibilities.

Advantageously, the means for analyzing liquid and/or gas flows are means for analyzing the fuel, the engine lubrication oil, the exhaust gas, the inlet air, the various post-treatment reagents and catalysts, the engine cooling fluid and the brake fluid.

Advantageously, the device includes means for analyzing the same liquid or gaseous flow at various places.

And it can be considered to measure a flow upstream and downstream of a process (example: gas post-treatment), so as to check the correct operation of the process.

Advantageously, the device is provided with means for receiving instructions for managing the analysis means from the engine computer.

Advantageously, the analysis means are powered by a common power supply.

Advantageously, the device includes a common electronic or digital system for driving the analysis means.

Advantageously, the device includes a common system for the electric power supply of analysis means.

In one embodiment, the analysis means include a common light source for analyzing the liquid and/or gas flows.

In a second embodiment, the analysis means include a common detector for analyzing the liquid and/or gas flows.

In a third embodiment, each flow can be analyzed through a light source and a detector which are common for all the flows. In this case, the device includes a switch making it possible to sequentially analyze the liquid and/or gas flows. In one embodiment, the switch is a membrane or micro-mirror MEMS micro-mechanical switch which makes it possible to successively direct the light flow, and positioned between the source and the liquid and/or gas flows or between the liquid and/or the gas flows and the detector.

Thus, these various embodiments make it possible, in particular, to use the same light source and/or the same detector so as to group the various components in order to remedy the problems of bulk, integration and mass increase.

In a fourth embodiment, the analysis means include for each liquid and/or gas flow a distinct source and detector.

According to a second aspect, the invention relates to a vehicle equipped with a management device according the first aspect of the invention.

Other objects and advantages of the invention will appear upon reading the following description and referring to the appended drawings.

BRIEF DESCRIPTION OF THE DRAWINGS

These and other sample aspects of the disclosure will be described in the detailed description and the appended claims that follow, and in the accompanying drawings, wherein:

Figure 1:
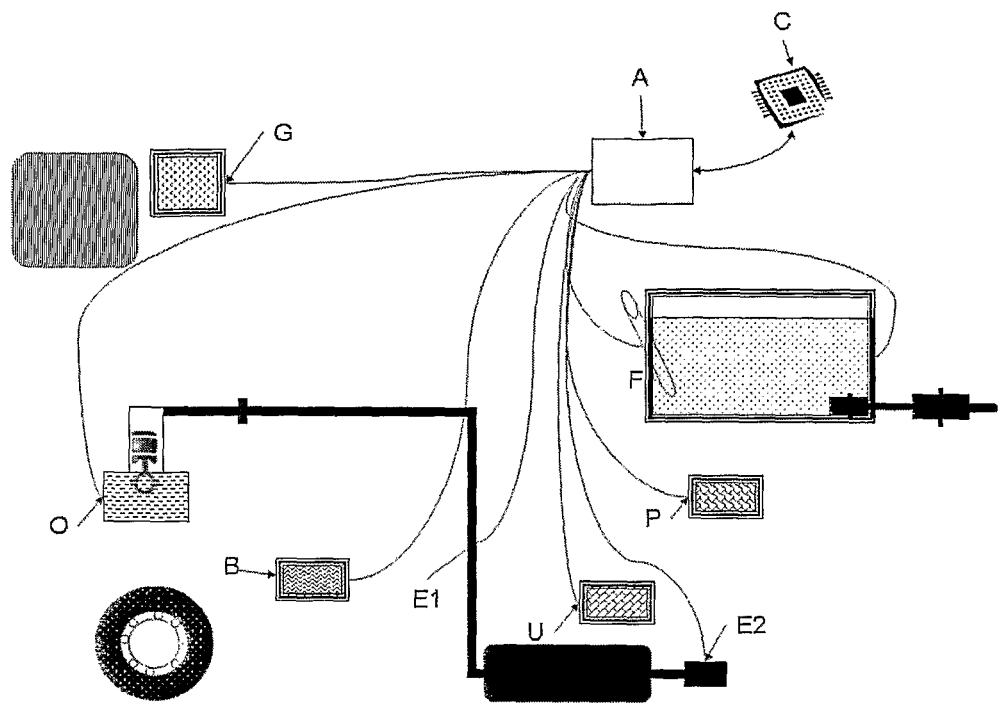
FIG. 1 is an example diagram illustrating a fluid verification system, in accordance with aspects of the present invention.

In accordance with common practice, the various features illustrated in the drawings may be simplified for clarity. Thus, the drawings may not depict all of the components of a given apparatus or method. In addition, like reference numerals may be used to denote like features throughout the specification and figures.

DETAILED DESCRIPTION

FIG. 1 describes an overview of a system making it possible to analyze various fluids (F, P, U, B, O, G) needed for the correct operation of a combustion engine and a vehicle from a centralized analyzer (A) connected to the various samples through optical fibres. Such centralized analyzer (A) makes it possible to use some electronic and/or optical components in common.

The supply of the source or sources and the detector or detectors for example can be unique. The same light source and/or the same detector can also be used for collecting the ultraviolet, visible and near infrared spectra of the various fluids.

The casing including such analyzing system is in common too. The connector technology and interface of the centralized analyzer with the computer in charge of the engine control (C) make it possible to convey information on the quality measured for each of the various fluids are unique.

The electronic or digital system in charge of driving the centralized analyzer and/or determining the quality of the various fluids from the near infrared spectra thereof can also be unique.

Such a device for centralising the measures and information on quality aboard thus has the advantage of minimizing the bulk and added mass induced by the addition of a sensor.

In the embodiment shown, the analysis means are positioned for analyzing the fuel (F), the engine lubrication oil (O), the exhaust gas (E2), the inlet air (E1), the various post-treatment reagents and catalysts (U, P), the engine cooling fluid (B) and the brake fluid (G).

Figure 2:
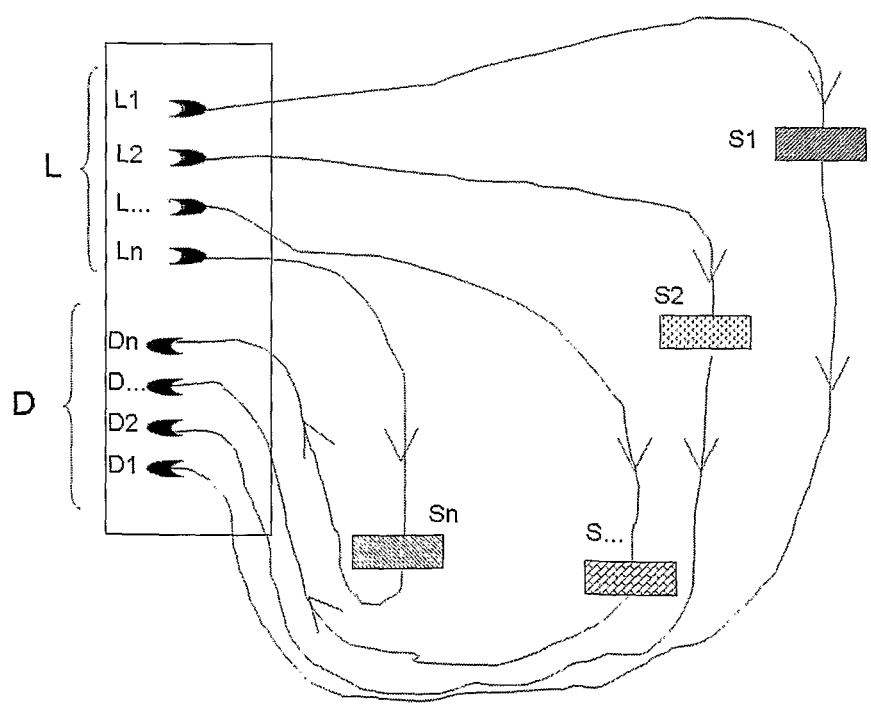
FIG. 2 is an example diagram illustrating an optical architecture, in accordance with aspects of the present invention.

FIG. 2 describes a particular embodiment of an optical architecture making it possible to use several light sources (L1, L2, Ln) and several detectors (D1, D2, Dn). The light beam coming from each one of the various light sources (L1, L2, Ln) is directed into optical fibres or into separate strands of optical fibres. The light at the output of each optical fibre or of the strand of optical fibres goes through a distinct sample (S1, S2, S . . . , Sn) of the fluid needed for the correct operation of the engine and/or of the vehicle.

The beam of light transmitted at the output of each distinct fluid sample is then directed to detectors (D1, D2, Dn) proper to each analyzed fluid, either through an optical fibre or directly.

Figure 3:
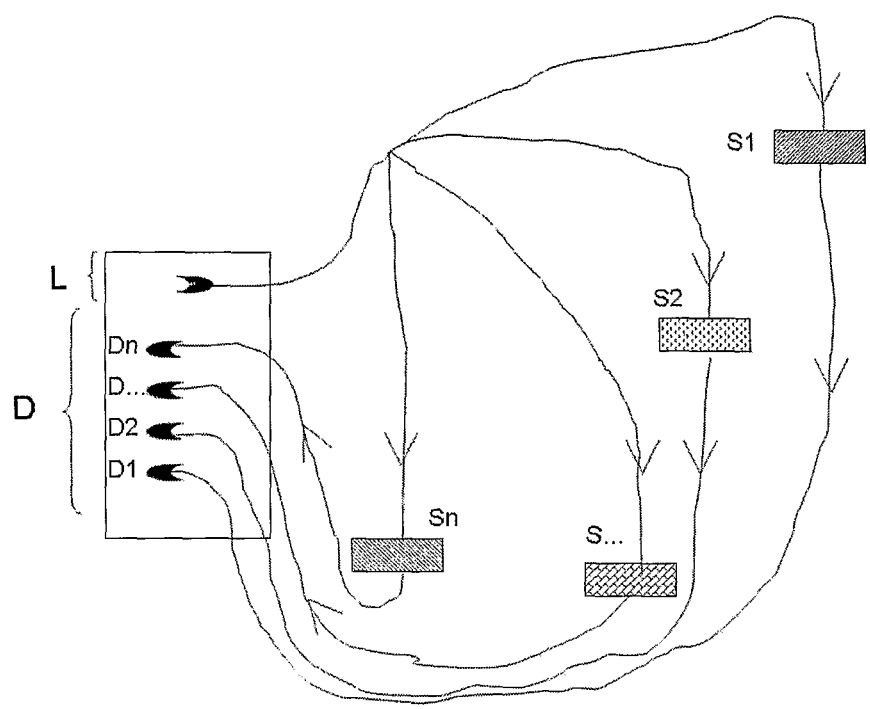
FIG. 3 is an example diagram illustrating an optical architecture, in accordance with aspects of the present invention.

FIG. 3 describes a particular embodiment of an optical architecture making it possible to use a common light source (L) and several detectors (D1, D2, D . . . , Dn).

The light coming from the common light source (L) is directed to an optical fibre or a common strand of optical fibres. The light flow is then split and each part is directed towards the various systems for sampling the various fluids (S1, S2, S . . . , Sn) required for the correct operation of the combustion engine and/or the vehicle. The light transmitted through each sample of distinct fluids is then directed to detectors (D1, D2, D . . . , Dn) proper to each analyzed fluid, either through an optical fibre or directly.

This particular architecture has the advantage, with respect to the one described in FIG. 2, to minimize the bulk resulting from the light sources as well as to minimize the potential problems connected with the alignment between the sources and the fibres or the sources and the detectors.

Figure 4:
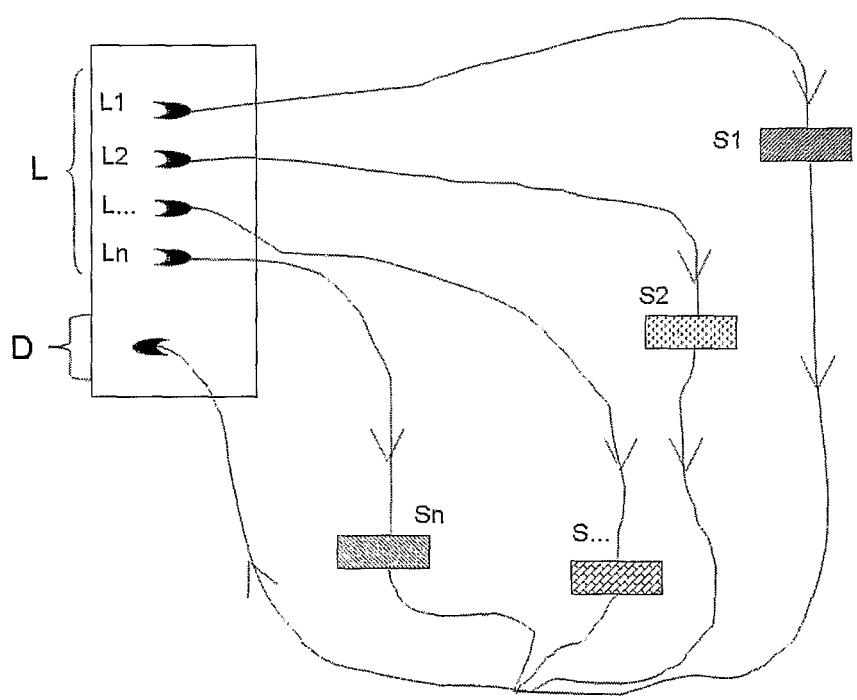
FIG. 4 is an example diagram illustrating an optical architecture, in accordance with aspects of the present invention.

FIG. 4 describes a particular embodiment of an optical architecture making it possible to use several light sources (L1, L2, Ln) and only one common detector (D).

The light coming from each one of the various light sources (L1, L2, Ln) is directed to optical fibres or distinct strands of optical fibres. The light emitted by each optical fibre or strand of optical fibres goes through a distinct sample of the fluids (S1, S2, Sn) needed for the correct operation of the engine and/or the vehicle. The light transmitted through such sample of fluid is then directed to a common detector (D).

This particular architecture has the advantage, with respect to the one described in FIG. 2, to minimize the bulk of the detectors and to minimize the potential problems relating to the alignment between the detectors and the fibres.

Figure 5:
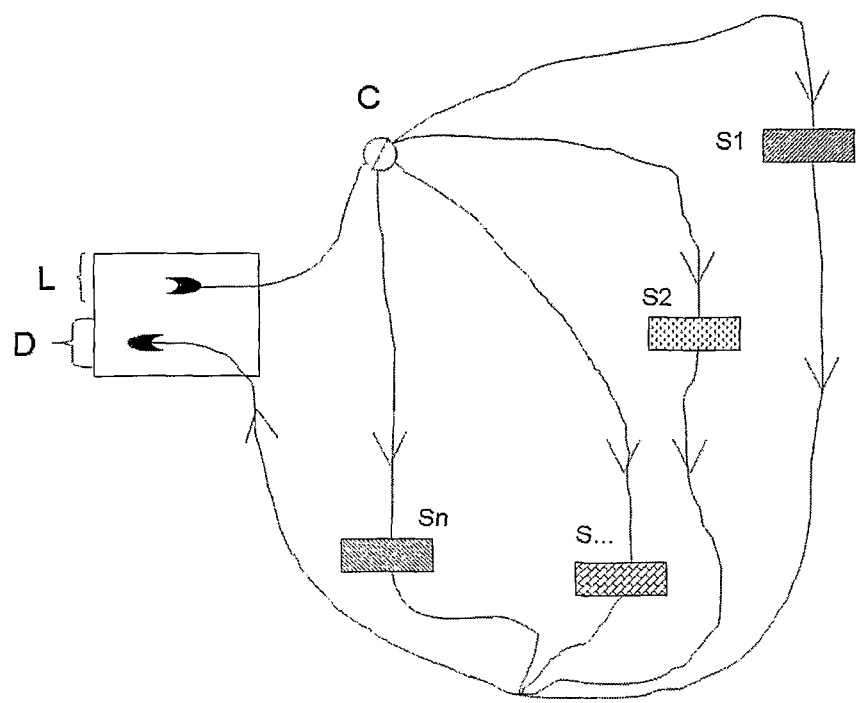
FIG. 5 is an example diagram illustrating an optical architecture, in accordance with aspects of the present invention.

FIG. 5 describes a particular embodiment of an optical architecture making it possible to use a common light source (L) and a common detector (D).

The light coming from the common light source (L) is directed into an optical fibre or a common strand of optical fibres. The optical fibre or the strand of optical fibres is then split and each part is directed to the various systems for sampling the various fluids needed for the correct operation of the combustion engine and/or the vehicle. The light flow is directed to a particular flow through a switch (C) of the mobile membrane or micro-mirror MEMS micro-mechanical type. The light emitted goes through a particular sample of one of the fluids (S1, S2, S . . . , Sn) needed for the correct operation of the engine and/or the vehicle. The light transmitted through such fluid sample is then directed to a common detector (D). The driving switch (C) makes it possible to select the fluid to be analyzed.

Such a particular architecture has the advantage, with respect to those described in FIGS. 2, 3 and 4 to minimize the bulk resulting from the detectors and resulting from the light sources as well as to minimize the potential problems relating to the alignment between the light sources and the fibres or between the detectors and the fibres.

Figure 6:
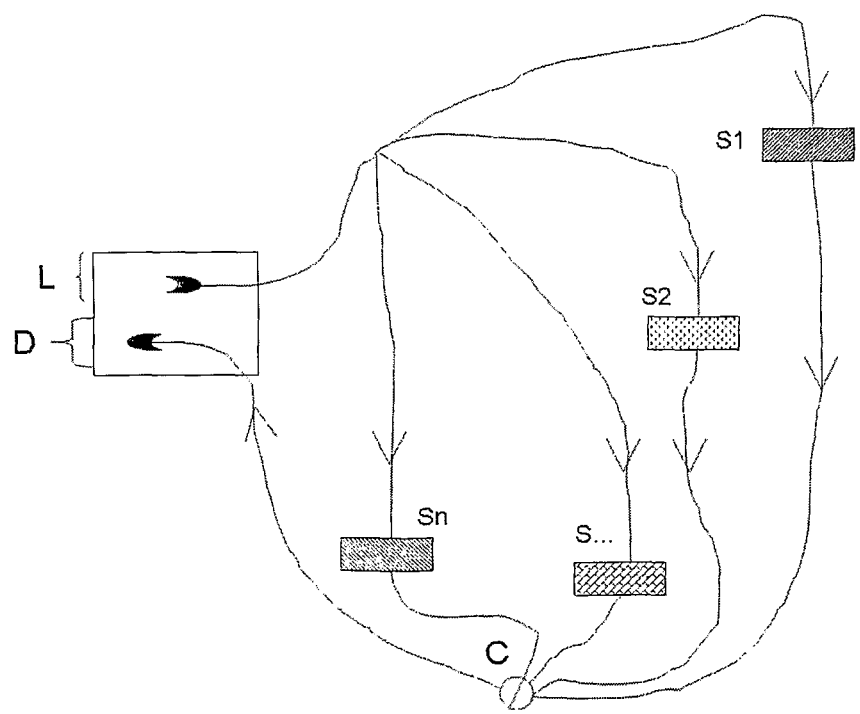
FIG. 6 is an example diagram illustrating an optical architecture, in accordance with aspects of the present invention.

FIG. 6 describes a particular embodiment of an optical architecture making it possible to use a common light source (L) and a common detector (D).

The light emitted by the common light source (L) is directed into an optical fibre or a common strand of optical fibres. The light flow is then split and each part is directed to the various systems for sampling the various fluids (S1, S2, S . . . , Sn) needed for the correct operation of the combustion engine and/or the vehicle. The light transmitted through each sample of distinct fluid is then directed to a switch (C) of the mobile membrane or micro-mirror MEMS micro-mechanical switch type making it possible to select the light flow to be transmitted to the common detector (D). Driving the switch (C) makes it possible to select the fluid to be analyzed.

This particular architecture has the same advantages as the architecture described in the particular embodiment of FIG. 5.

The architectures described in FIGS. 2 and 3 make it possible to simultaneously analyze the various flows.

The architectures described in FIGS. 2 and 4 make it possible to analyze independently and sequentially each flow by driving (putting on/putting off) the various light sources.

The architectures described in FIGS. 5 and 6 make it possible to analyze independently and sequentially each flow by controlling the switch.

The architectures 2 and 3 have the flexibility of using or not optical fibres between the samples and the detectors.

The system for analyzing the detected signals is a computer programme managing the spectrometer. The programme is unique and common to the various flows. Such programme makes it possible to ensure the correct operation of the various modules (more particularly sources and detectors) of the system as well as acquiring the ultraviolet, visible and near infrared spectra of the various flows.

The programme making it possible to qualitatively characterise each flow from the ultraviolet, visible and near infrared spectra thereof will include the calibrations and mathematical or digital treatments proper to each one of the analyzed flows.

The interface between the analysis means and the engine control computer is centralized and common to the various analyzed fluids.

The engine control computer can control the triggering of a particular analysis, a sequence of analyses or a simultaneous analysis of the fluids.

The invention claimed is:

1. A device for the centralized management of measurements and data relating to liquid and/or gas flows needed for the correct operation of a combustion engine controlled by an engine computer, said device comprising optical architecture for analyzing at least one liquid flow and one gas flow comprising at least one light source, at least one optical signals detector and at least one system for analyzing the detected signals, said device being characterized in that the device is arranged on a vehicle;
    at least one of said at least one light source and said at least one optical signals detector is arranged to be used for analyzing two of said flows; and
    lengths of optical paths through samples of said liquid and gas flows vary with optical fibers.

2. The device according to claim 1, characterized in that the optical architecture is positioned on a single platform.

3. The device according to one of claim 1 or 2, characterized in that it includes a single interface for communicating with said engine computer, the physical and/or digital connector technology with the computer being common with the optical architecture.

4. The device according to any one of claim 1 or 2, characterized in that the optical architecture utilizes spectra selected from the group consisting of ultraviolet, visible, near infrared, and combinations thereof.

5. The device according to claim 4, characterized in that the ultraviolet, visible and near infrared spectroscopic analysis is continuous or discontinuous and is carried out within the wavelength range between 190 nm and 2,500 nm.

6. The device according to claim 1, characterized in that the liquid and/or gas flows being analyzed are selected from the group consisting of fuel, engine lubrication oil, exhaust gas, inlet air, various post-treatment reagents and catalysts, engine cooling fluid, and brake fluid.

7. The device according to claim 1, characterized in that the optical architecture analyzes the same liquid or gas flow at various places.

8. The device according to claim 7, characterized in that the various flows are analyzed sequentially or simultaneously.

9. The device according to claim 1, characterized in that it is provided with a receiver for receiving instructions for managing the optical architecture from the engine computer.

10. The device according to claim 9, characterized in that the optical architecture is supplied by a common power supply.

11. The device according to claim 10, characterized in that it includes a common electronic or digital system for driving the optical architecture.

12. The device according to claim 1, characterized in that the optical architecture includes a common light source for analyzing the liquid and/or gas flows.

13. The device according to claim 12, characterized in that the optical architecture includes a common detector for analyzing the liquid and/or gas flows.

14. The device according to claim 13, characterized in that the light source and the detector are common to all the flows.

15. The device according to claim 14, characterized in that it includes a switch making it possible to sequentially carry out the analysis of the liquid and/or gas flows.

16. The device according to claim 15, characterized in that the switch is a membrane or micro-mirror MEMS micromechanical switch making it possible to successively direct the light flow and positioned between the source and the liquid and/or gas flows or between the liquid and/or the gas flows and the detector.

17. The device according to claim 1, characterized in that the optical architecture includes, for each liquid and/or gas flow, a distinct source and detector.

18. A vehicle characterized in that is it provided with the management device according to claim 1.

* * * * *